US00PP28217P3

(12) United States Plant Patent
Mazzardis

(10) Patent No.: US PP28,217 P3
(45) Date of Patent: Jul. 25, 2017

(54) BLUEBERRY PLANT NAMED 'EB 10-1'

(50) Latin Name: ***Vaccinium* hybrid**
Varietal Denomination: EB 10-1

(71) Applicant: Vincent David Mazzardis, Joondalup (AU)

(72) Inventor: Vincent David Mazzardis, Joondalup (AU)

(73) Assignee: Bisa Trading Pty. Ltd., Cannington, Western Australia ( * ) Notice: Subject to any disclaimer, the term of this patent is extended or adjusted under 35 U.S.C. 154(b) by 23 days.

(21) Appl. No.: 14/756,642

(22) Filed: Sep. 28, 2015

(65) Prior Publication Data

US 2016/0113171 P1 Apr. 21, 2016

(30) Foreign Application Priority Data

Oct. 16, 2014 (AU) ..... PBR 2014/246

(51) Int. Cl.
*A01H 5/08* (2006.01)

(52) U.S. Cl.
USPC ..... Plt./157

(58) Field of Classification Search
USPC ..... Plt./157
See application file for complete search history.

(56) References Cited

FOREIGN PATENT DOCUMENTS

AU 2014/246 10/2014

OTHER PUBLICATIONS

Plant Varieties Journal, vol. 28, Issue 1, Published Jun. 15, 2015.

*Primary Examiner* — Susan McCormick Ewoldt
(74) *Attorney, Agent, or Firm* — Randall Danskin P.S.

(57) ABSTRACT

A new and distinct variety of blueberry plant, which is denominated varietally as 'EB 10-1' is described, and which produces large to very large fruit, which further has a fruit ripening date which is very late in the season when grown under the ecological conditions prevailing near Yanchep Springs, Western Australia.

1 Drawing Sheet

Botanical designation: '*Vaccinium* Hybrid'.
Varietal denomination: 'EB 10-1'.

RELATED APPLICATION DATA

The present application claims priority to Australian Plant Breeders Rights Application, Serial No. 2014/246, and which was filed on Oct. 16, 2014, and which further was further accepted on Dec. 23, 2014.

BACKGROUND OF THE NEW VARIETY

The present invention relates to a new, common, novel and distinct variety of blueberry plant '*Vaccinium* hybrid' and which has been denominated varietally as 'EB 10-1'.

ORIGIN AND ASEXUAL REPRODUCTION OF THE NEW VARIETY

The present variety of blueberry plant resulted from an ongoing development program of plant breeding. The purpose of this program was to improve the commercial quality of various plant varieties by creating, and releasing, promising selections of plants, including blueberries. To this end, I have made both controlled, and hybrid cross-pollinations each year to produce resulting plant populations from which improved progenies are evaluated and selected.

The blueberry plant 'EB 10-1' was derived from a controlled cross-pollination employing the blueberry plant '7-13' [unpatented], and which was the seed parent, and blueberry plant '7-30', [unpatented], and which was the pollen parent, during the 2007 growing season, and which further took place at Yanchep Springs, Yanchep, Western Australia. The seed parent '7-13' is characterized by an upright, bush-type of growth habit; displays a mid-season flowering date; and further produces large, firm fruit. The pollen parent, on the other hand, is characterized by a semi-upright growth habit; displays a mid to late season flowering date; and further produces medium to large fruit. The seed derived from the seed parent, blueberry plant '7-13', produced approximately 1,000 plants. These new plants were then grown, and the first fruit was evaluated during the 2009 growing season. Further, an additional assessment of these same new plants took place in 2010. At this time the promising new variety 'EB 10-1' was selected for further asexual reproduction, and evaluation. The present variety was asexually reproduced by cuttings and the plants produced from this first asexual propagation were again evaluated during the 2011 to 2014 growing seasons. The asexually reproduced plants which were evaluated were true to the original plant, and it was my conclusion, at that time, that variety 'EB 10-1' was a new, novel and distinct variety of blueberry plant. The asexual reproduction of Blueberry Plant EB-10-1 occurred at Yanchep Springs, Yanchep Western Australia.

In relative comparison to one of the closest known varieties, that being the 'Ridley 1111' blueberry plant which is further identified as U.S. Plant Pat. No. 23,572 and which was filed on Jan. 18, 2011, the new variety of blueberry plant is clearly distinguishable by its large to very large fruit size when compared to the average size fruit produced by the "Ridley 1111' blueberry plant. Further, the present variety was distinguishable from the 'Ridley 1111' in view of its early fruit ripening date. In this regard the 'Ridley 1111' blueberry plant is ripe for harvesting approximately middle to late in the season. Still further, the present variety is distinguishable from its seed and pollen parents in view of its large to very large fruit. This is in contrast to the seed parent which merely produces large fruit, and the pollen parent which produces medium-large fruit. In relative comparison to another closely similar variety, that being the blueberry plant 'EB 8-46' which is further identified as U.S. Plant Pat. No. 26,173 and which was filed on Nov. 21, 2013, the new blueberry variety is distinguishable therefrom in view of date of its vegetative bud burst, its earlier flowering date, and the time of the beginning of fruit ripening. These plant characteristics are all considered medium to late in the season. These plant distinctions will be further discussed in the paragraphs which follow. The new variety of blueberry plant 'EB 10-1' is characterized as the novelty by producing a semi-upright to intermediate bush-type growth habit, large to very large, and slightly flat fruit, and wherein the fruit has an excellent bloom, and flavor and further has a very late season flowering and fruit maturity date. The new variety is also distinguishable from a closely similar blueberry variety, 'EB 8-17' which is further identified as U.S. Plant Pat. No. 25,860 and which was filed on Jun. 12, 2013. The new and present variety of blueberry plant is distinguishable therefrom in view of its medium to late date in the season for its beginning of flowering; the time of the displayed vegetative bud burst; and fruit ripening time on one year old shoots. In this regard, the blueberry variety 'EB 8-17' expresses a very early date in the growing season for the same growth characteristics. These plant characteristics will be discussed in the paragraphs which follow.

BRIEF DESCRIPTION OF THE DRAWINGS

The accompanying drawing is a color photograph which shows the new blueberry plant 'EB 10-1', at an age of two years, juxtaposed relative to an image of one of the closest-known varieties, that being, the blueberry plant 'EB 8-46'.

The photograph depicts several mature fruit which are sufficiently mature for harvesting and shipment, and further shows typical shoot-bearing leaves, and at least one leaf showing the dorsal coloration thereof, and the fruit produced by the new variety.

The photograph also shows the same parts of the plant for one of the closest-known varieties 'EB 8-46'.

The colors in the attached photograph are as nearly true as reasonably possible in a color representation of this type. Due to chemical development, processing and printing, the leaves and fruit depicted in this photograph may or may not be accurate when compared to the actual specimens. For this reason, future color references should be made to the descriptions as provided, hereinafter.

The photograph of EB 10-1 and the photograph of EB 8-46 provided for visual comparison are not taken on the same scale. The photo of EB 10-1 has been "cropped" so that the photographs may be aligned side-by-side, and the "cropping" incorrectly resulted in an appearance that the plant and fruit of EB 10-1 are smaller than their true size.

NOT A COMMERCIAL WARRANTY

The following detailed description has been prepared to solely comply with the provisions of 35 U.S.C. §112, and does not constitute a commercial warranty, (either expressed or implied), that the present variety will, in the future, display the botanical, horticultural, or other characteristics as set forth, hereinafter. Therefore, this disclosure may not be relied upon to support any future legal claims including, but not limited to, breach of warranty and merchantability, or fitness for any particular purpose, or non-infringement which is directed, in whole, or in part, to the present variety.

DETAILED DESCRIPTION

Referring more specifically to the botanical details of this new and distinct variety of blueberry plant, the following has been observed during the sixth growing season under the ecological conditions prevailing at the farm of the inventor, and which is located near Yanchep Springs, Western Australia.

The age of the plant at the time of the description that follows herein is three (3) years.

The colors and codes used herein to describe the EB 10-1 plant, refer to The Royal Horticultural Society (R.H.S.) Colour Chart. 5$^{th}$ Ed. 2007.

PLANT

Plant vigor: The present variety of blueberry plant is considered to display a medium to strong plant vigor. This is similar to the closest-known variety 'EB 8-46' which was first mentioned above.

Plant growth habit: The new variety of blueberry plant has a semi-upright to intermediate growth habit. This is somewhat in contrast to the seed parent which has an upright, bush-type growth habit, and the pollen parent which expresses a semi-upright growth habit.

Color, one year old shoots: Yellow Green N144C (R.H.S. Colour Chart, 5$^{th}$ Ed. 2007).

Internode length:

*One year old shoots*.—Considered long for the species, about 17 mm. This is in contrast to the closest-known variety, 'EB 8-46', and which has an average internode length.

Height of plant at time of description herein is: Three years.

Width of plant at time of description is: Three years.

Bark color is: Greyed Orange. 174B (R.H.S. Colour Chart, 5$^{th}$ Ed., 2007).

LEAVES

Leaf length:

*Generally*.—Considered long for the species, about 72.97 mm. This is in contrast to the closest known varieties 'EB 8-46' and 'EB 8-17' (now U.S. Plant Pat. No. 26,173 and now U.S. Plant Pat. No. 25,860 respectively), and where the average length of the leaves of these closely similar blueberry varieties are 60.33 mm, and 66.07 mm, respectively.

Leaf width:

*Generally*.—Considered narrow to average in width, about 33 mm. This is in contrast to the closest known variety 'EB 8-17', and which has an average leaf width of about 35.53 mm; and the leaf width of the blueberry plant 'EB 8-46', and which has an average leaf width of about 34.1 mm.

Leaf ratio:

*Length/width.*—Considered large. This is in contrast to the closest known blueberry variety 'EB 8-46', and which is considered merely average.

Leaf shape: Ovate.

Leaf color:

*Dorsal surface.*—Yellow Green N146A (R.H.S. Colour Chart, 5th Ed. 2007).

Leaf color: Under Surface is Yellow Green N148A (R.H.S. Colour Chart, 5th Ed. 2007).

Seed color: Is Greyed Orange 163C (R.H.S. Colour Chart, 5th Ed. 2007).

Leaf color intensity:

*Dorsal surface.*—Considered an average green color as compared to the closest known variety 'EB 8-17', and which is considered to display a medium to dark green color.

Leaf marginal edge: Entire.

Texture of the leaf is: Glabrous.

Shape of the leaf is: Elliptic.

Leaf apex shape is: Acute.

Leaf apex base shape is: Acute.

Vein color of the leaf is: Yellow Green 144A (R.H.S. Colour Chart, 5th Ed. 2007).

Venation pattern of the leaf is: Pinnately reticulate.

Leaf arrangement is: Alternate.

FLOWERS

Flower bud coloration: The presence of anthocyanin is considered very weak in the flower buds.

Inflorescence length: Considered average to long, about 22 mm.

Corolla shape: Urceolate.

Corolla tube size: Considered average.

Corolla tube coloration: Any anthocyanin coloration is considered absent or very weak.

Corolla tube ridges: Present.

Color of opened flower is: White 155B (R.H.S. Colour Chart, 5th Ed. 2007).

Average number of flowers per inflorescence is: 15.

Corolla texture is: Rigid.

Corolla length is: About 13.8 mm.

Corolla diameter is: About 11.6 mm.

Corolla color is: White 155c (R.H.S. Colour Chart, 5th Ed. 2007).

Corolla aperture size is: About 6.6 mm.

Pedicle length is: About 11.8 mm.

Pedicle color is: Yellow Green 145C (R.H.S. Colour Chart, 5th Ed. 2007).

Date of bud burst is: July.

Bloom time is: July-August.

Bloom duration is: About six weeks.

FRUIT

Fruit cluster density: Medium to dense for the species.

Unripe fruit color is: Yellow Green 150B (R.H.S. Colour Chart, 5th Ed. 2007).

Fruit size: Considered large to very large, about 23.12 mm. This is in contrast to the closest known varieties 'EB 8-17', and which has an average fruit diameter of about 19.88 mm; and that of blueberry plant 'EB 8-46' which expresses an average fruit diameter of about 19.57 mm.

Fruit shape when viewed in a longitudinal section: Considered oblate.

Sepal position/attitude: Considered semi-erect.

Sepal type: Generally considered incurving.

Calyx basin diameter: Considered large, about 10.12 mm. This is in contrast to the closest known varieties 'EB 8-17' and 'EB 8-46' which each have a Calyx basin width (diameter) of about 8.22 mm, respectively.

Fruit height: On average the new variety of blueberry plant has a fruit height of about 14.40 mm. This is in contrast to the closest known variety 'EB 8-17', and which has a fruit height of about 13.61 mm.

Calyx basin depth: Considered shallow for the species, about 2.79 mm. This is in contrast to the closest known variety 'EB 8-46', and which has a Calyx basin depth of about 3.38 mm.

Fruit weight: About 5.64 gm. This is in contrast to the closest known variety 'EB 8-46', and which has an average fruit weight of about 3.79 gm.

Fruit:

*Intensity of bloom.*—Considered strong to very strong.

Fruit skin color: Black 203C (R.H.S. Colour Chart, 5th Ed. 2007).

Fruit flesh color (ripened fruit) is: Yellow Green 1500 (R.H.S. Colour Chart, 5th Ed. 2007).

Fruit firmness: Considered firm.

Fruit sweetness: Considered high for the species.

Fruit acidity:

*Generally.*—Considered very low to low.

Plant fruiting type: Generally speaking fruiting occurs on one year old, and current season's shoots.

Time of vegetative bud burst: Considered medium to late in the season. This is in contrast to the closest known variety, 'EB 8-46', and where the same characteristics are expressed early in the season. Further, and in contrast, the blueberry plant 'EB 8-17', expresses this same growth characteristic very early in the growing season.

Beginning of flowering on one year old shoots: Considered medium to late in the growing season (approximately July-August). Again, this is in contrast to the closest known variety, 'EB 8-46', and where this plant characteristic occurs early in the season, and that of the blueberry plant 'EB 8-17', and where this plant characteristic occurs very early in the season.

Beginning of flowering on current year's shoots: Considered medium to late in the season (approximately July-August). Again, this is in contrast to the closest known variety 'EB 8-46', and where this plant characteristic occurs early in the season; and the same growth characteristic as expressed by the blueberry plant 'EB 8-17', and which occurs very early in the season.

Beginning of fruit ripening on one year old shoots: Considered to be medium to late in the season. This is in contrast, again, to the closest known varieties 'EB 8-17' and 'EB 8-46', and where this same growth characteristic is expressed very early or early in the season, respectively.

Beginning of fruit ripening on current year's shoots: Considered to be medium to late in the season. Again, this is in contrast again to the closest known varieties 'EB 8-17' and 'EB 8-46' and where this growth characteristic occurs either very early or early in the season, respectively.

Reproductive organs of the plant:

*Size of the pollen anthers is.*—Approximately 4.7 mm.

*Color of the pollen anthers is.*—Greyed Orange 165B (R.H.S. Colour Chart, 5th Ed. 2007).

*Pistil length l is*.—Approximately 7.2 mm.

*Pistil color is*.—Green 147C (R.H.S. Colour Chart, 5$^{th}$ Ed. 2007).

*Market use of the fruit is*.—First Grade Fresh Market Fruit.

*Pollination requirement is*.—Self-fertile.

Fruit productivity:

*Average weight of fruit per plant is*.—About 5.64 g.

*Storability of the plant fruit is*.—Considered to be a long.

*The observed date of the first pick is*.—Approximately November.

*The observed date of the last pick is*.—Approximately January.

Resistance to insects and diseases: No particular susceptibilities were noted. The present variety has not been tested to expose or detect any susceptibilities or resistance to any known plant and/or fruit diseases.

Although the new variety of blueberry plant possesses the described characteristics when grown under the ecological conditions prevailing near Yanchep Springs, Western Australia, it should be understood that the variations of the magnitude and characteristics incident to changes in growing conditions, fertilizations, pruning, pest control, frost, climatic variables and horticultural management are to be expected.

Having thus described and illustrated my new variety of blueberry plant, what I claim is new, and desire to secure by plant Letters Patent is:

1. A new and distinct variety of blueberry plant, substantially as illustrated and described, and which is characterized principally as to novelty by producing a large to very large fruit, which has an excellent fruit flavor and a medium to late fruit ripening date, when grown under the ecological conditions prevailing near Yanchep Springs, Western Australia.

* * * * *

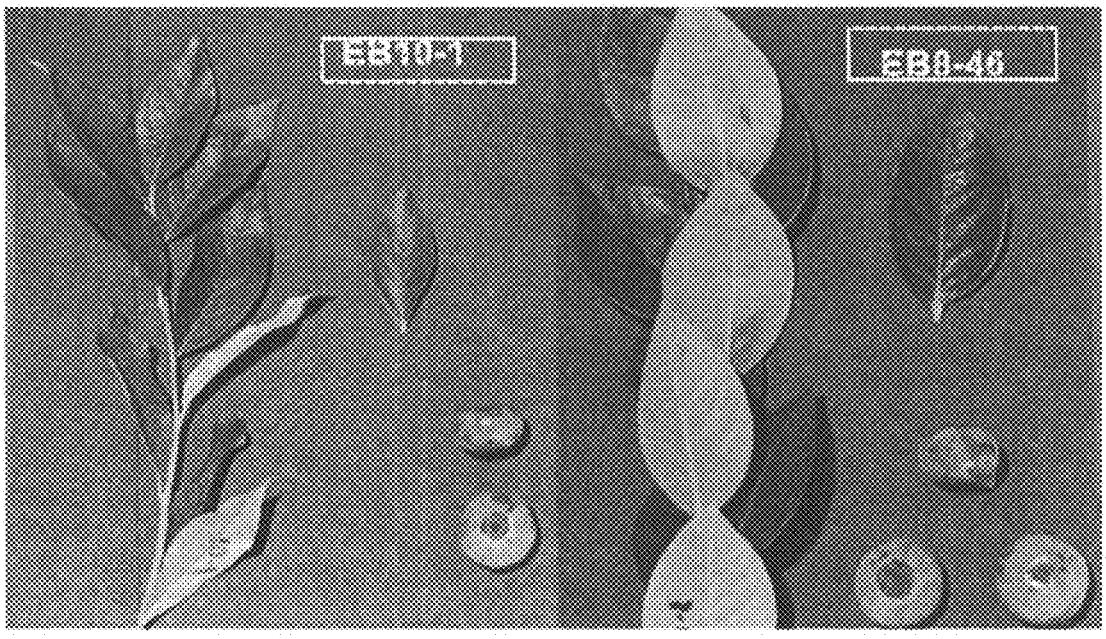
EB10-1
EB8-46